US009655573B2

United States Patent
Majewski et al.

(10) Patent No.: US 9,655,573 B2
(45) Date of Patent: May 23, 2017

(54) VIRPET—COMBINATION OF VIRTUAL REALITY AND PET BRAIN IMAGING

(71) Applicant: West Virginia University, Morgantown, WV (US)

(72) Inventors: Stanislaw Majewski, Charlottesville, VA (US); Julie Brefczynski-Lewis, Morgantown, WV (US)

(73) Assignee: WEST VIRGINIA UNIVERSITY, Morgantown, WV (US)

( * ) Notice: Subject to any disclaimer, the term of this patent is extended or adjusted under 35 U.S.C. 154(b) by 0 days.

(21) Appl. No.: 14/969,597

(22) Filed: Dec. 15, 2015

(65) Prior Publication Data
US 2016/0166219 A1    Jun. 16, 2016

Related U.S. Application Data
(60) Provisional application No. 62/091,790, filed on Dec. 15, 2014.

(51) Int. Cl.
*A61B 6/00*    (2006.01)
*A61B 6/03*    (2006.01)
*A61B 34/30*    (2016.01)

(52) U.S. Cl.
CPC ............ *A61B 6/4405* (2013.01); *A61B 6/037* (2013.01); *A61B 6/462* (2013.01); *A61B 6/466* (2013.01);
(Continued)

(58) Field of Classification Search
CPC ... G01R 33/4806; A61B 5/024; A61B 5/4064; A61B 5/107; A61B 5/7271;
(Continued)

(56) References Cited

U.S. PATENT DOCUMENTS 5,546,943 A * 8/1996 Gould ................. G06F 19/3437
                                                    128/898
6,674,083 B2    1/2004 Tanaka et al.
(Continued)

OTHER PUBLICATIONS

Yamamoto et al."Development of a Brain PET System, PET-Hat: A Wearable PET System for Brain Research", IEEE Transactions on Nuclear Science, vol. 58, No. 3, Jun. 2011.
(Continued)

*Primary Examiner* — David Porta
*Assistant Examiner* — Faye Boosalis
(74) *Attorney, Agent, or Firm* — Thomas | Horstemeyer LLP; Scott A. Horstemeyer; Randy R. Schoen

(57) ABSTRACT

Various methods, systems and apparatus are provided for brain imaging during virtual reality stimulation. In one example, among others, a system for virtual ambulatory environment brain imaging includes a mobile brain imager configured to obtain positron emission tomography (PET) scans of a subject in motion, and a virtual reality (VR) system configured to provide one or more stimuli to the subject during the PET scans. In another example, a method for virtual ambulatory environment brain imaging includes providing stimulation to a subject through a virtual reality (VR) system; and obtaining a positron emission tomography (PET) scan of the subject while moving in response to the stimulation from the VR system. The mobile brain imager can be positioned on the subject with an array of imaging photodetector modules distributed about the head of the subject.

20 Claims, 12 Drawing Sheets

(52) U.S. Cl.
CPC .............. *A61B 6/501* (2013.01); *A61B 34/30* (2016.02); *A61B 6/467* (2013.01); *A61B 6/5205* (2013.01)

(58) Field of Classification Search
CPC ....... A61B 6/5235; A61B 6/12; A61B 6/4028; A61B 6/4405; A61B 6/037
See application file for complete search history.

(56) References Cited

U.S. PATENT DOCUMENTS

| | | |
|---|---|---|
| 7,884,331 B2 | 2/2011 | Majewski et al. |
| 9,226,717 B2 * | 1/2016 | Tashima ................. A61B 6/037 |
| 2013/0211238 A1 * | 8/2013 | DeCharms ........... A61B 5/4824 600/418 |
| 2015/0306340 A1 * | 10/2015 | Giap ....................... A61B 5/05 600/301 |

OTHER PUBLICATIONS

Tashima et al.,"A proposed helmet-PET with a jaw detector enabling high-sensitivity brain imaging", 2013 IEEE Nuclear Science Symposium and Medical Imaging Conference (NSS/MIC), Oct. 2013.

* cited by examiner

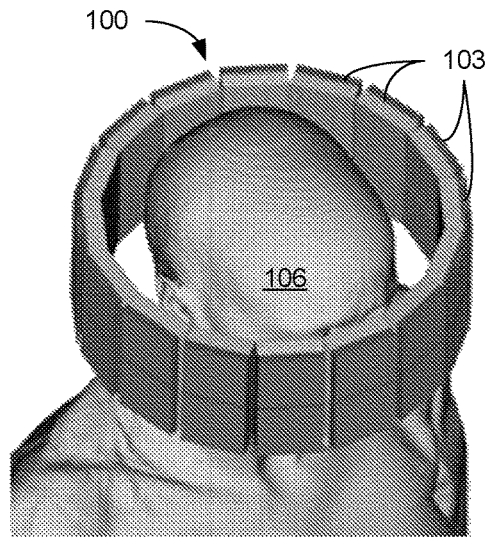
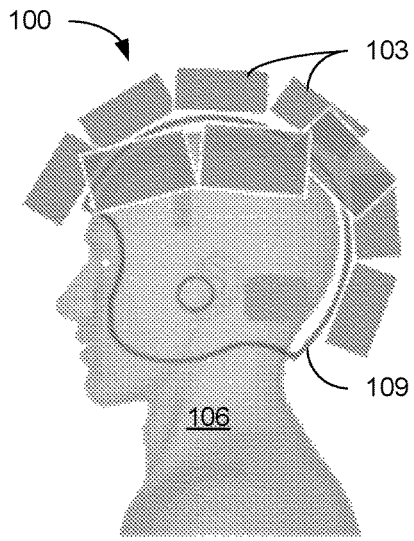
FIG. 1A  FIG. 1B
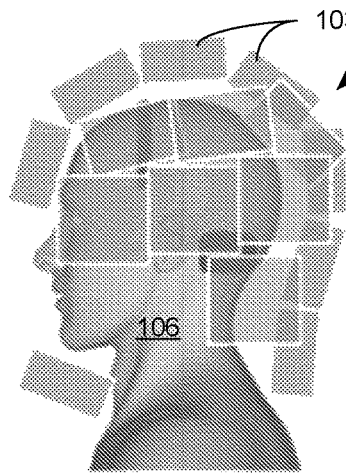
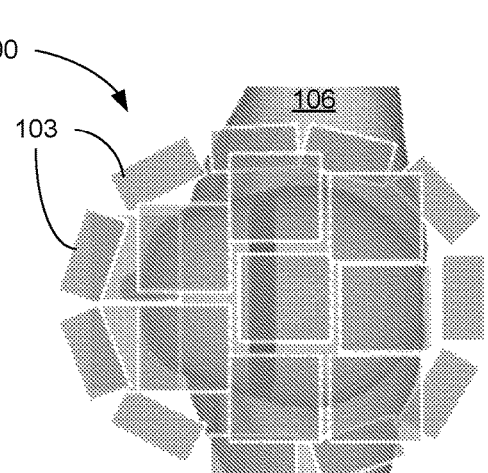
FIG. 1C  FIG. 1D

VIRPET—COMBINATION OF VIRTUAL REALITY AND PET BRAIN IMAGING

CROSS REFERENCE TO RELATED APPLICATIONS

This application claims priority to, and the benefit of, co-pending U.S. provisional application entitled "ViR-PET—Combination of Virtual Reality and PET Brain Imaging" having Ser. No. 62/091,790, filed Dec. 15, 2014, which is hereby incorporated by reference in its entirety.

STATEMENT REGARDING FEDERALLY SPONSORED RESEARCH OR DEVELOPMENT

This invention was made with government support under agreement DE-AC05-06OR23177 awarded by the Department of Energy. The Government has certain rights in the invention.

BACKGROUND

Positron emission tomography (PET) is a well-established molecular imaging modality. Current clinical PET scanners are large, bulky devices that are placed in dedicated imaging rooms and require the subject to be brought to the imager. With very few exceptions, PET scanners are typically limited to imaging subjects in a supine or prone position. They are also typically combined with CT scanners, which are not easily amenable to other than horizontal imaging geometries. Functional magnetic resonance imaging (fMRI) cannot be used for functional brain imaging of upright subjects, because present day upright MRI scanners do not provide strong enough magnetic field for functional imaging. In addition, MRI requires that the subject be immobile during the scan.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 1A through 1F are examples of mobile brain imagers of a virtual ambulatory environment brain imaging system in accordance with various embodiments of the present disclosure.

DETAILED DESCRIPTION

Figure 1E:
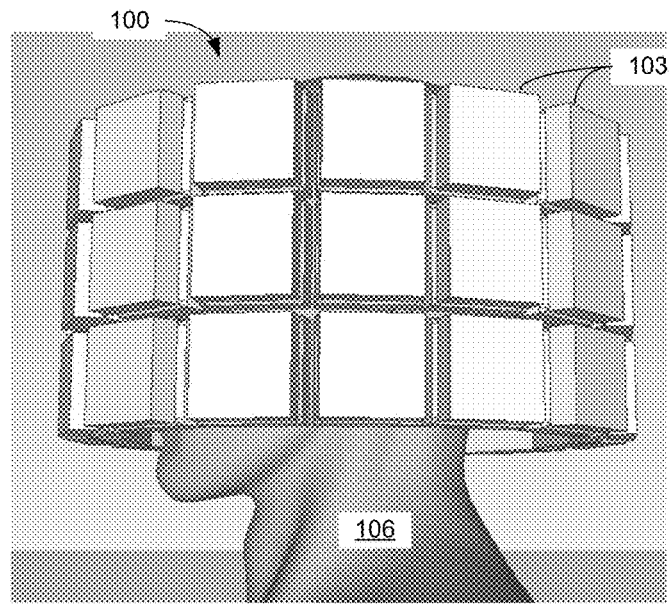

Disclosed herein are various examples related to virtual ambulatory environment brain imaging. The virtual ambulatory environment allows subjects to be studied while in motion (e.g., walking, running, or other bodily movements). The logistical and safety issues related to imaging the brain of a moving subject can also be reduced by using the virtual ambulatory environment. Reference will now be made in detail to the description of the embodiments as illustrated in the drawings, wherein like reference numbers indicate like parts throughout the several views.

Many functional processes in the human brain depend on the subject's position and/or interaction with the surrounding environment. Examples include imaging brains of patients who are undergoing post-stroke motor function impairment therapy while upright (standing) and/or exercising (e.g., on a treadmill, balancing platform, etc.). In addition, for patients who cannot be still such as those with cognitive deficits (e.g., autism, Alzheimer's disease, schizophrenia) or those with physical issues that prevent them from keeping still such as tremors, low dose imaging studies can provide insight into the brain function recovery and/or proscriptive personalized medicine/treatments plans in these patients. Also, subjects who exhibit the so-called "savant syndrome", or those with behavioral expertise or abilities could be imaged while performing relevant tasks, and conversely, those with negative behaviors such as PTSD or addition could be imaged in a more immersive environment, with either glucose or oxygen uptake or specific targeted neurotransmitter receptor availability. Currently, electroencephalography (EEG), magnetoencephalography (MEG) or near-infrared spectroscopy (NIRS) techniques can be used in these individuals when in the upright position, but these modalities do not provide full coverage of the brain during activity. In addition, these imaging modalities do not provide accurate high resolution molecular images of the brain.

An ambulatory brain imaging system using a wearable mobile brain imager can allow scanning and/or imaging to be carried out with the subject in supine, prone, or inclined positions, as well as in upright positions such as, e.g., sitting, standing, walking on treadmill, etc. Positron emission tomography (PET) is a high resolution functional brain imaging modality that can be used in upright subjects who can move or turn their heads. An ambulatory microdose PET (AMPET) imaging system can adapt to whole body movement of the subject. Combining PET with electroencephalography (EEG) and near infrared spectroscopy (NIRS) can enhance the functional information gathered with the brain immersed in the particular simulated environment. In fact, a combination of some or all of these modalities (e.g., PET/NIRS, PET/EEG, and/or PET/EEG/NIRS) can form the wearable mobile brain imager.

When used in conjunction with a virtual reality system, the impact of stimuli from and/or interactions with the surrounding environment can be examined. The virtual reality system can be implemented using video goggles, display screens or other visual means such as mirrors, projection screens, etc. In one embodiment of the system, the imager covers the eyes of the subject/patient to increase the sensitivity. To provide comfort to the subject/patient, as well as to deliver the stimulus of the VR environment, compact goggles with cameras for both eyes can be inserted between the detector and the eyes. A mobility platform can be used to allow the subjects or patients to be in motion or in various positions during the imaging. Position and/or movement of the subject or patient can be monitored to provide feedback to the virtual reality system and/or the brain imager. The effect of a virtual ambulatory environment on the functioning of the brain can be close to the stimulation experienced by the human brain during real world situations, while eliminating logistical issues, controlling variables, and improving safety during imaging with the subject in motion. In addition, the virtual reality environment can be used to intensify the external stimuli on the brain by providing more intense environment for the subject/patient to be immersed in with expected enhanced impact on the functions of the brain. This can have for example important implications in virtual therapy.

How much the human brain will be tricked into believing that the surrounding environment is "real" will depend on the quality of the virtual reality environment (e.g., the visual and sound gear, the software, speed of response, etc.) and also on the mobility platform. To enhance the realistic impressions on the body and thus the brain, the subject can be also subjected to physical stimuli such as, e.g., blowing and/or changing air flow ("wind"), temperature changes, painful stimuli, tactile stimuli, smells, and/or artificial rain or snow, in addition to the visual and audio effects. Multiple physical sensory impacts can enhance the "realism" of the virtual ambulatory environment.

With reference to FIGS. 1A-1F, shown are examples of compact and mobile brain imagers of brain imaging systems in accordance with various embodiments of the present disclosure. The mobile brain imager 100 can include imaging photodetector modules 103 that are placed around and close to the head of the subject or patient 106, or arranged as a set of individual imaging photodetector modules 103 surrounding the head of the subject or patient 106 in an irregular tight pattern. For example, the mobile brain imager 100 can include one or more rings (e.g., 1-4 rings) of imaging photodetector modules 103 for viewing the brain of a subject or patient 106. In FIG. 1A, the imaging photodetector modules 103 form two rings composed of 16 closely spaced and individually read imaging modules 103. The rings of imaging photodetector modules 103 can provide surface coverage and angular views for high resolution 2D/3D PET image slice reconstruction of the brain.

A semi-spherical geometry can improve the solid angle coverage, which can provide a higher sensitivity. In FIGS. 1B-1D, the imaging photodetector modules 103 are positioned in groupings of tiles that tightly cover the head of the subject or patient 106. The imaging photodetector modules 103 can be placed behind and/or above the head, and/or under the chin, to increase the detection efficiency especially in the central regions of the brain. The arrangement of the imaging photodetector modules 103 is typically a tight fit to the head to maximize sensitivity of the mobile brain imager 100. The imaging photodetector modules 103 operate in a coincidence mode between all pairs in the set, as in a standard PET system. A light weight, but rigid support structure can support the imaging photodetector modules 103 in a precise hemispherical arrangement.

Figure 1F:
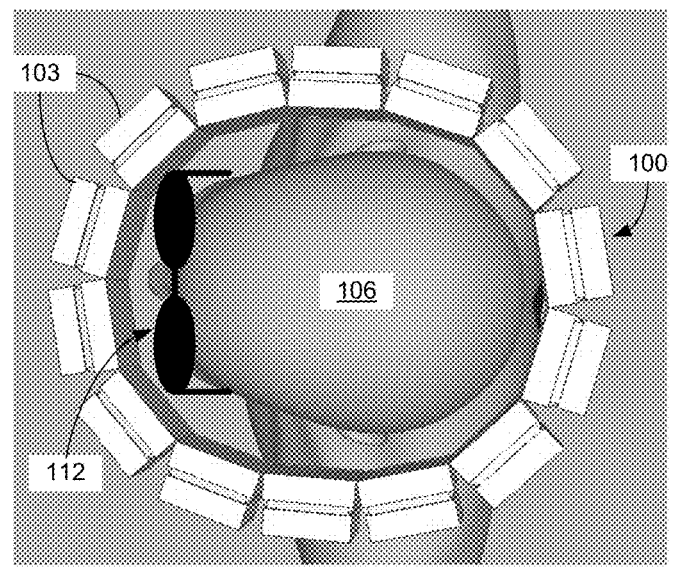

FIGS. 1E and 1F illustrate a mobile brain imager 100 with imaging photodetector modules 103 that extends over the eyes of the subject/patient 106 to increase the sensitivity. Multiple rows of photodetector modules 103 (e.g., three as shown in FIG. 1E) can extend downward from the crown of the head. To provide comfort to the subject/patient 106, compact goggles 112 with cameras for both eyes can be inserted between the photodetector modules 103 and the eyes of the subject/patient 106.

The imaging photodetector modules 103 include a scintillator to produce gamma rays and a coupled photodetector to detect the scintillation light produced by the absorbed gamma rays. The scintillator can comprise pixelated or plate crystal scintillator materials such as, e.g., LSO, LYSO, GSO, BGO, LaBr3, NaI(Tl), CsI(Tl), and/or CsI(Na). The photodetector can comprise, e.g., a standard or multi-element photomultiplier (PMT), avalanche photodiode (APD) arrays or large size APD, and/or other silicon photomultipliers (SiPM). For example, fast scintillators such as LYSO and fast electronics can be used to exploit the time of flight (TOF) characteristics of PET imaging. The TOF information improves the sensitivity and uniformity of response, especially in the "set of modules" variant with limited angular coverage, and can reduce the artifacts in PET reconstruction images that are caused by the incomplete angular sampling. High resolution TOF can provide substantial remedy in addition to depth of interaction (DOI) information. A timing resolution of 100-350 psec full width at half maximum (FWHM) is useful in such a compact system, with sub-200 psec timing resolution being desirable.

The imaging photodetector modules 103 can be mounted in or on a lightweight helmet 109 with an opening for the head and neck as in FIG. 1B. The helmet 109 can include a ring or other arrangement of imaging photodetector modules 103 attached to an inner shell or liner. To maximize the efficiency and minimize the injected doses, the imaging photodetector modules 103 should be as close as possible to the head of the subject. A chin strap can be used to hold the assembly in position on the head of the subject or patient 106. The attached imaging photodetector modules 103 can be covered by an outer cover or shell, which can also encase other electronic circuitry associated with the mobile brain imager 100. The outer cover can be configured to accommodate a harness or tether to attach the assembly to an external support mechanism for mechanical support. A head registration cap can be used to provide a kinematic registration to the head of the subject, in addition to a comfortable fit for the helmet 109. The registration cap may be adjusted to accommodate the size and/or geometry of the head. A rigid and repeatable mount can be included on the registration cap to attach it to the imaging photodetector modules 103. Two axes of adjustment between the registration cap and the imaging photodetector modules 103 can be provided to allow for imaging of selectable portions of the brain.

Figure 2A:
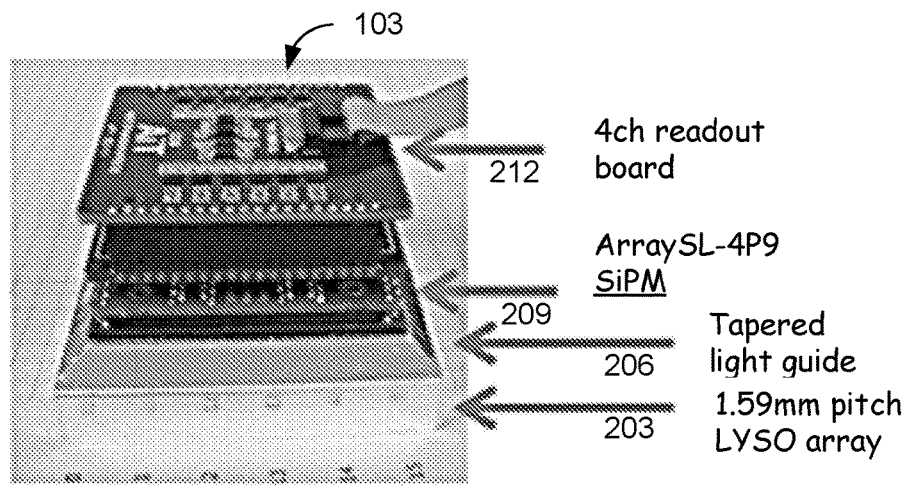
FIGS. 2A and 2C are examples of imaging photodetector modules of a mobile brain imager of FIGS. 1A-1F in accordance with various embodiments of the present disclosure.
Figure 2B:
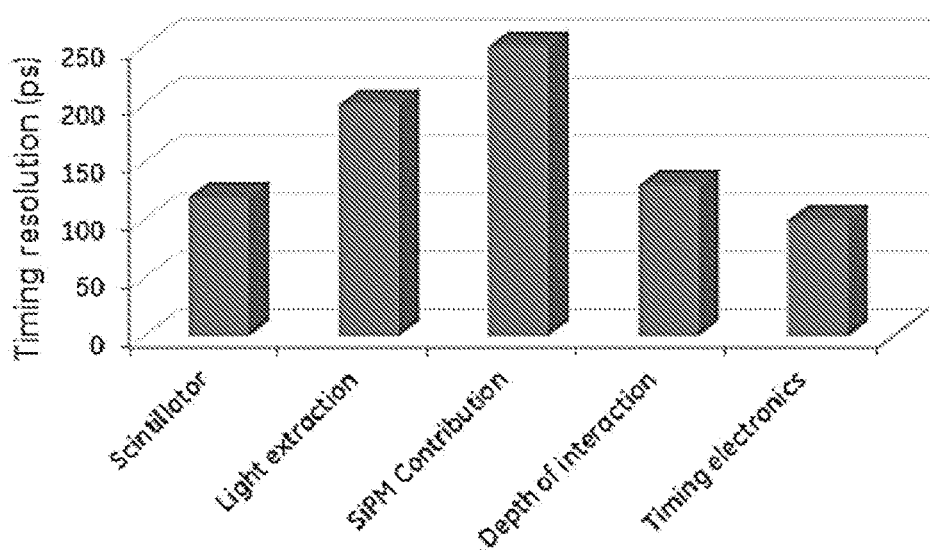
FIGS. 2B and 2D illustrate characteristics of the imaging photodetector modules of FIGS. 2A and 2C in accordance with various embodiments of the present disclosure.

Referring to FIG. 2A, shown is an image of an example of an individual compact PET imaging photodetector module 103. The imaging photodetector module 103 includes a scintillator array 203 with a thickness in the range of 10-25 mm. The scintillator array 203 is coupled through a light guide 206 to a silicon photomultiplier (SiPM) array 209. A readout board 212 interfaces with the SiPM 209 to provide measurement information via a plurality of readout channels (e.g., 4-32). In one embodiment, among others, a PET imaging photodetector module 103 includes Hamamatsu multi-pixel photon counter (MPPC) solid state photodetector technology coupled to arrays of LYSO pixels with 1.5 mm pitch and 10 mm thick from Proteus. Twelve modules of about 5 cm×5 cm coverage each are arranged in a ring geometry with about 21 cm face-to-face inner diameter. A charge division readout from AiT Instruments that employed 4 channels per module was implemented. The 48 amplified detector signals were digitized in the FPGA USB2 64ch DAQ module of integrating ADCs developed at Jefferson Lab and available from AiT Instruments. A 16-ch Mesytec MCFD-16 trigger module produced the coincidence trigger for the DAQ module between any pair of the 12 ring modules. Read-out software was implemented using Java programming language with an overlaying user interface provided by a Kmax scientific programming package from Sparrow Corporation. FIG. 2B is a graph illustrating an example of the overall timing resolution (380 ps) of a SiPM based PET imaging photodetector module 103. As can be seen in FIG. 2B, all subcomponents of the module 103 contribute in varying degrees to the overall performance.

Figure 2C:
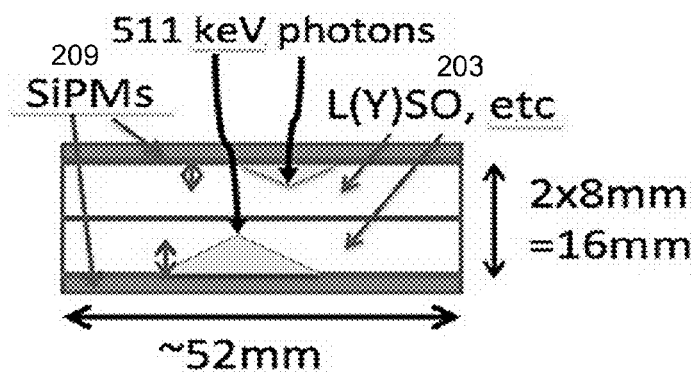
Figure 2D:
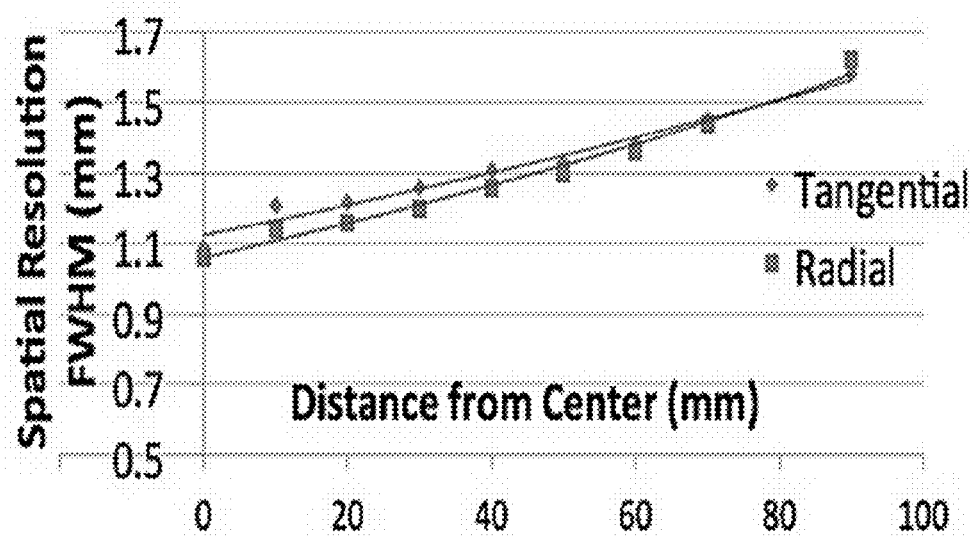

FIG. 2C is a cross-sectional view of an example of a module assembly that can be used to increase the light detection efficiency of the PET imaging photodetector module 103. The module assembly can include two monolithic slabs of scintillator 203 with dual end readout using SiPMs 209. Use of the dual end readout with the use of maximum likelihood algorithms can maximize the timing. Simulation results shown in FIG. 2D show that a resolution of approximately 1 mm is achievable in the center. Closer integration of the electronics and the imaging photodetector modules 103, and on-chip signal processing algorithms, can improve the timing and spatial information.

A compact and mobile high resolution brain imaging system can provide tomographic slice reconstruction and a 3D reconstruction resolution. The tight geometry of the imaging photodetector modules 103 about the head of the subject 106 can create response non-uniformity and reconstruction problems. Special tomographic reconstruction can be used to deal with the compactness of the geometry and breaks between the individual imaging photodetector modules 103, producing limited angular coverage with regular (rings) or irregular (set of modules) breaks. A data acquisition (DAQ) electronics module can be located in a mobile container or cabinet with, e.g., a cable connection between the imaging photodetector modules 103 and the DAQ module. In some implementations, the DAQ electronics module can wirelessly communicate with the imaging photodetector modules 103. An on-board computing system can produce reconstructed 3D images in a short time after the end of each imaging session (e.g., a few minutes or less). The brain imaging system can record data to enable limited data analysis, fast data replay, and image reconstruction during the same scan session.

An image reconstruction application, executed by a computing system, can be used to generate the images from the data from the imaging photodetector modules 103. Accurate system response matrices can be determined for adjustments or variations in the geometric configuration of the imaging photodetector modules 103. The imaging photodetector modules 103 can be pre-characterized using a single-photon response function (SPRF). The SPRF represents the probability of a photon that enters the front face of the imaging photodetector module 103 at position (x,y) with polar and azimuthal angles ($\phi,\theta$) being detected by crystal i of the imaging photodetector module 103. The SPRF can be computed analytically or determined through simulation using a collimated point source, and stored in memory.

For a pair of imaging photodetector modules 103 in the wearable brain imager 100, the SPRFs can be used to form the coincidence response function for a line projection based on the position and incidence angle of the line projection with respect to each imaging photodetector module 103. The computation can be performed very quickly as it can involve only multiplications of the elements in the SPRFs. In this way, a sinogram blurring matrix can be produced that represents the probability of a pair of photons emitted along the line projection being detected by any detector pairs. Using the SPRF, the geometric projection matrix and sinogram blurring matrix can be decoupled. The geometric projection matrix can be computed on-the-fly using ray-tracing methods. Combination of the geometric projection matrix and sinogram blurring matrix can provide an accurate system model for PET image reconstruction.

Factors affecting PET image quality include attenuation, scattered and random coincidences, detector efficiency variations, system dead-time, and/or system-wide deadtime. For attenuation correction, TOF-based correction methods can be used. Simulations can be used to evaluate the accuracy of this approach for the 100-200 ps timing resolutions. This approach may be supplemented with other techniques that start with the non-attenuation-corrected PET image. Quantitative corrections can also be implemented for scatter, randoms, detector efficiency normalization and deadtime. For scatter, a Bergstrom convolution approach can be used due to the simple attenuation geometry. A Klein-Nishina based estimation method may also be utilized. For randoms, singles based correction methods, which are based upon characterization of detector dead-time, can be used. Dead-time can be measured for both distributed and focal source geometries, and fit to a singles-rate model. Many industry dead-time models are among the most sophisticated available. For correction of detector efficiency variations, a component-based normalization procedure that decouples detector related factors, such as crystal efficiencies, block effects, and timing profile, from geometric factors can be used.

Figure 3A:
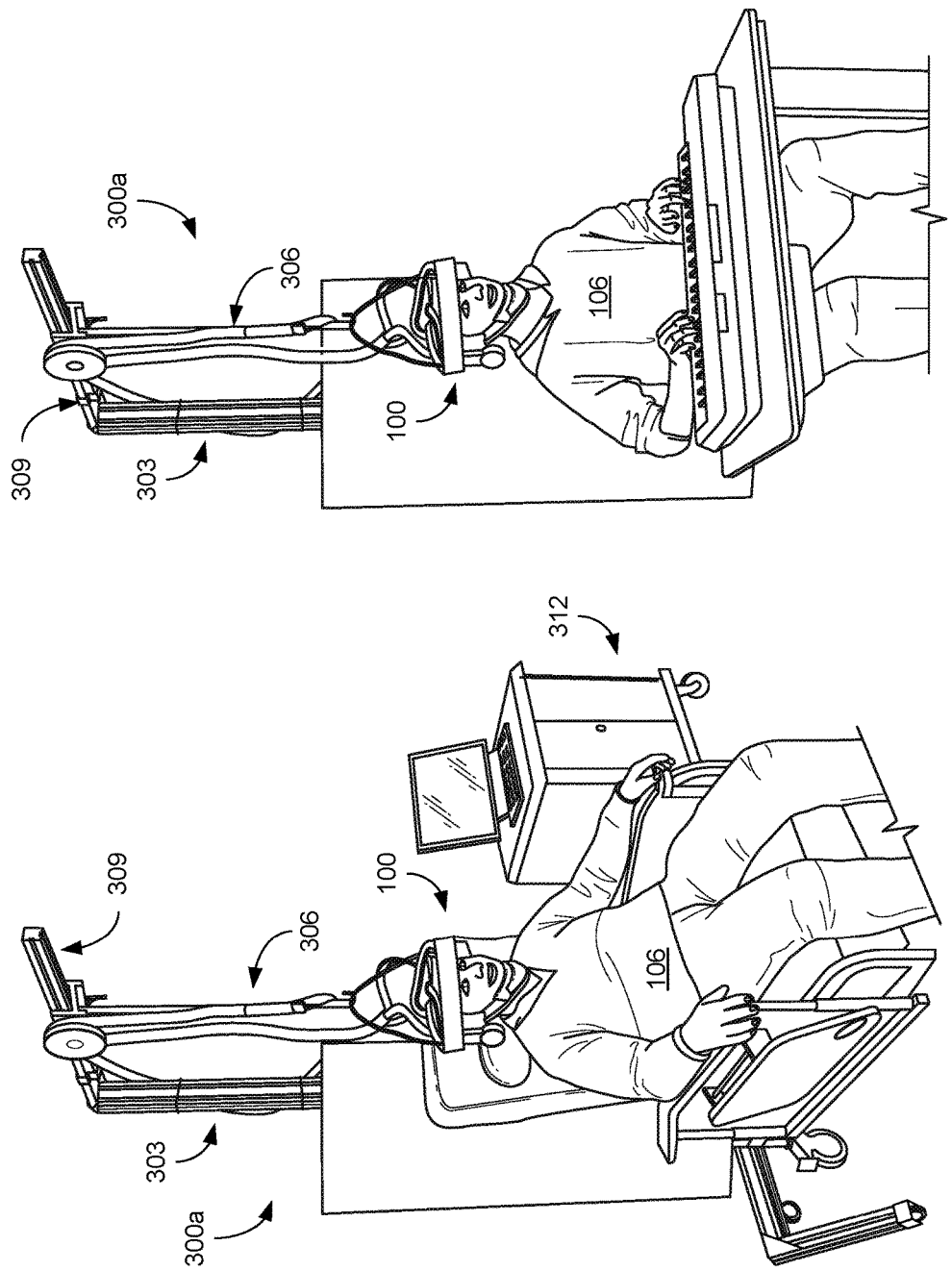
FIGS. 3A through 3C are examples of support systems for the mobile brain imagers of FIGS. 1A-1F in accordance with various embodiments of the present disclosure.

The brain imaging system can provide safe, reliable and comfortable co-registration of the imaging photodetector modules 103 with the head and/or brain of the subject 106, while allowing the subject 106 to freely move during use. Referring to FIG. 3A, shown are images of a support system 300a that allows freedom of movement of the subject 106. In the example of FIG. 3A, the mobile brain imager 100 is suspended from a mobile overhead support frame 303 by a tether 306 (or other flexible support) that extends downward from a support boom 309 of the overhead support frame 303. The mobile brain imager 100 can be suspended from a rolling support on a spring or counterbalance to enable more flexible and comfortable placement of the mobile brain imager 100, and can be adjusted vertically on the subject's head to image the desired part of the brain. The tether 306 can be secured to the overhead support frame 303 at one end and clipped to the mobile brain imager 100 at the other end, and can be elastic to allow for movement of the subject 106. The design can also permit the mobile brain imager 100 to become detached from the overhead support frame 303. Wired connections from the imaging photodetector modules 103 to a computing system 312 of the ambulatory brain imaging system can also be supported by the support boom 309 of the overhead support frame 303. While the subject 106 is shown sitting down in FIG. 3A, the support system 300a can be adjusted to accommodate movement while the subject 106 is standing.

Figure 3B:
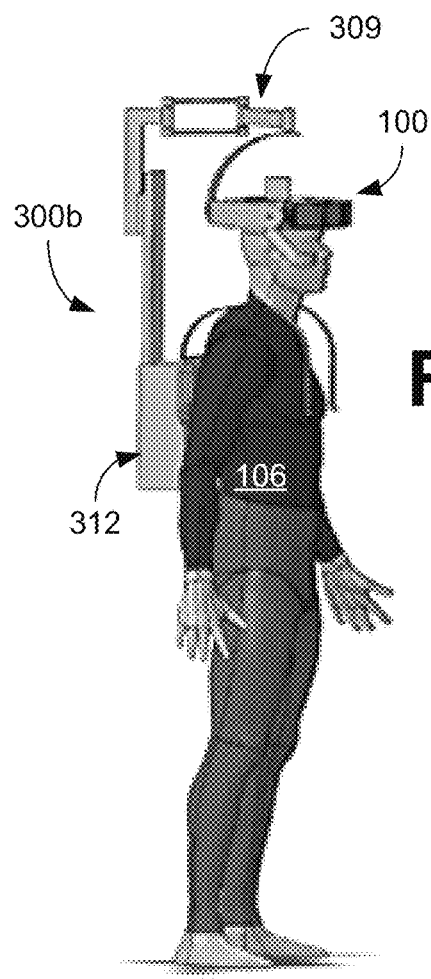

FIG. 3B illustrates another example of a support system 300b that allows the subject 106 to move freely while wearing the mobile brain imager 100. The self-contained backpack support system 300b can be worn by the subject 106 is shown in FIG. 3B. A support boom 309 can be used to transfer the weight of the mobile brain imager 100 to the support system 300b through a tether or other flexible support, when it is placed on the head of the subject or patient 106. A gimbal mechanism can be used to apply a counterbalance force to neutralize the weight of the mobile brain imager 100, while allowing for a full six degrees of freedom for the head. A light weight, low friction, and compact gimbal mechanism can minimize distraction of the subject 106. Wired connections between the imaging photodetector modules 103 and computing system 312 can also be supported by the support boom 309. In some embodiments, the computing system 312 and power supply can be included in the backpack support system 300b as illustrated in FIG. 3B. Data from the imaging photodetector modules 103 can be collected and stored by the computing system 312, and/or transferred to a local base station via a wireless connection. Hardware can manage the cables to avoid risk of electrical shock, excessive fiction and/or entanglement during movement. An emergency release of the mobile brain imager 100 may also be provided for safety of the subject 106.

Figure 3C:
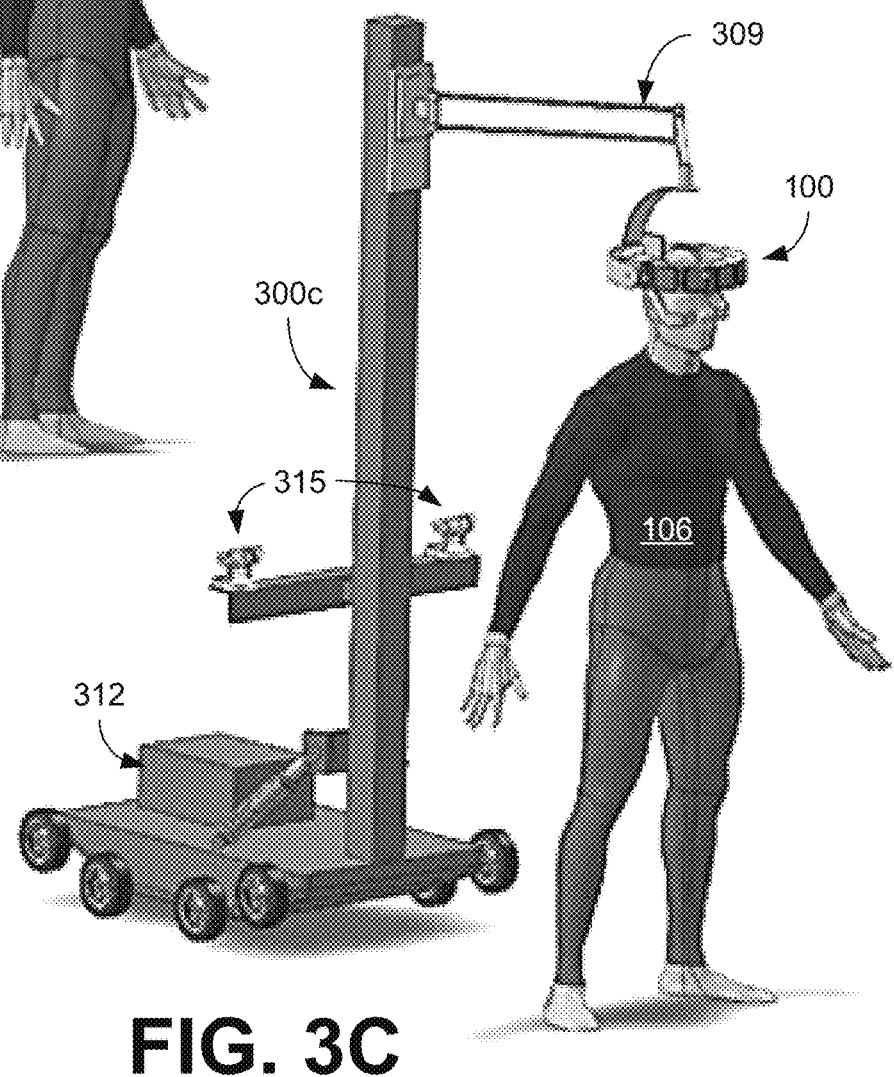

Referring to FIG. 3C, shown is a robotic support system 300c that moves ("walks" or rides) with the subject and provides a flexible counterbalancing support for the weight of the mobile brain imager 100, while minimizing the stress to the subject 106. As in FIG. 3B, a support boom 309 can be used to transfer the weight of the mobile brain imager 100 to the support system 300c. The support boom 309 can include pivot points (or hinges) to allow sections of the boom to swing with the movement of the subject or patient 106 and a gimbal mechanism can be used to neutralize the weight of the mobile brain imager 100, while allowing for a full six degrees of freedom for the head. Wired connections from the imaging photodetector modules 103 to a computing system 312 can also be supported by the robotic support system 300c. A computing system 312 and power supply can be supported by the robotic support system 300c as illustrated in FIG. 3C. The computing system 312 can also control the movement of the robotic support system 300c based upon indications from sensors 315 that monitor the movement of the subject 106.

When the mobile brain imager 100 is used in conjunction with a virtual reality (VR) system, the impact of stimuli from and/or interactions with the surrounding environment can be examined. The virtual reality system can be configured to simulate a variety of visual, auditory, olfactory and/or tactile stimuli. A VR control system can be used to control and coordinate the stimulations provided to the subject or patient 106. Visual stimulation can be implemented using visual interfaces including, but not limited to, video goggles, display screens or other visual means such as mirrors, projection screens, etc. Audio stimulation can be implemented using headphones, speakers, or other noise generating devices. Scent or odor generating devices can be used to provide olfactory stimulation. A variety of sources can be used to provide tactile or painful stimulation. For example, jet sprays and/or air nozzles can be used to simulate wet and/or windy conditions. Heat and/or cold can also be simulated by controlling the temperature of the air directed at the subject 106 or through the use of heating lamps. Haptic or tactile clothing can also be used to provide contact and/or pressure directly to the skin of the subject 106. Heating and/or cooling circuits or devices can also be included in clothing of the subject 106.

Figure 4A:
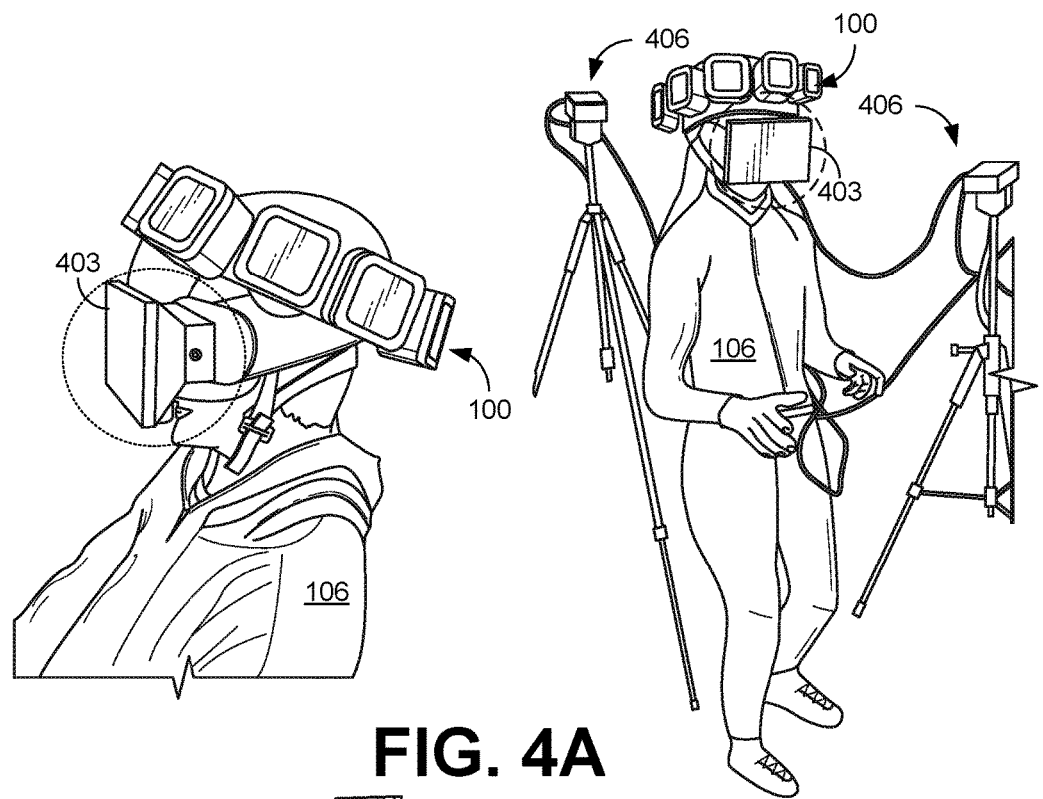
FIGS. 4A and 4B are examples of visual interfaces for a virtual reality system of the virtual ambulatory environment brain imaging system in accordance with various embodiments of the present disclosure.

As shown in FIG. 4A, subjects 106 wearing a mobile brain imager 100 can also wear video goggles 403 for visual stimulation during scanning and/or imaging. The goggles 403 can receive video or image inputs through a wired or wireless connection with the VR control system. Movement of the subject 106 can be monitored using, e.g., cameras 406, tactile clothing, or other monitoring device that detects the motion of the subject 106. The VR control system can monitor the movement and response of the subject 106 to the various stimuli, and adjust the stimulation in response. For example, the viewing perspective can be adjusted in response to head or body movement. Similarly, audio and/or tactile stimuli can be adjusted by the VR control system to account for changes in bodily orientation of the subject 106.

Figure 4B:
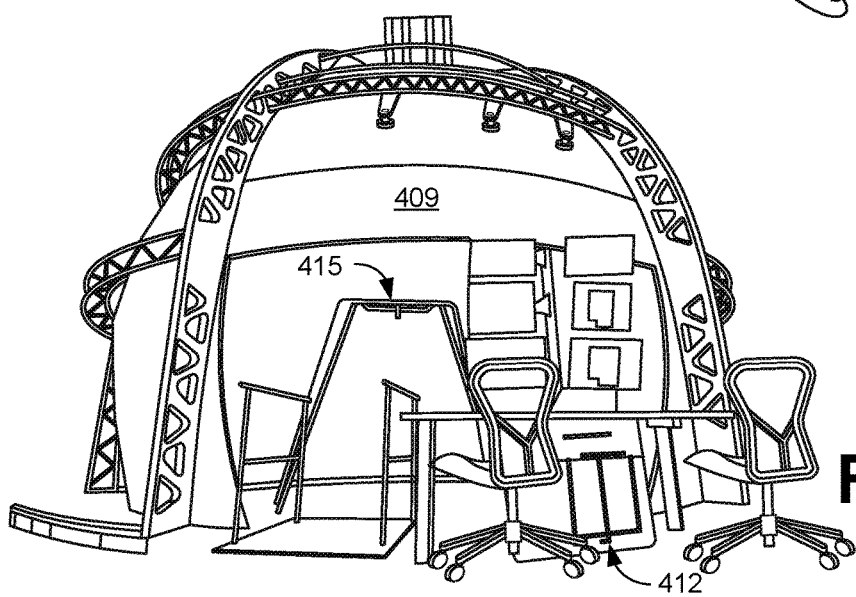

In some implementations, large displays or screens can be used instead of goggles 403. FIG. 4B shows an example of a virtual reality enclosure 409 that surrounds the subject or patient 106 with one or more display. Additional visual, audio, olfactory and/or tactile simulation sources can be integrated into the VR enclosure 409. For example, controllable lighting, speakers, air jets, water jets, etc. can be included to enhance the perception of the subject 106. The VR enclosure 409 can also include cameras and/or other sensors for monitoring the subject's movement and/or reaction to the stimuli. The VR control system 412 can control the various stimuli in response to the actions and/or reactions of the subject 106.

Figure 5A:
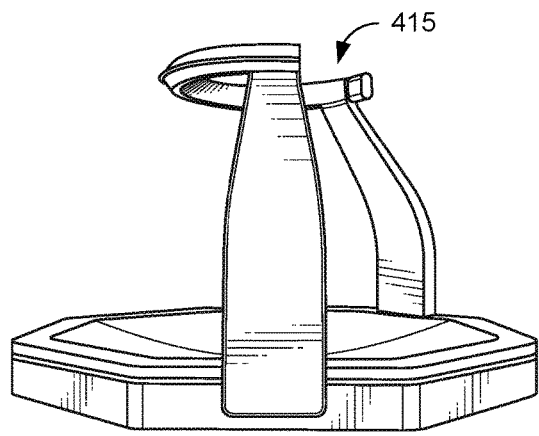
FIGS. 5A through 5C illustrate an example of a mobility platform for the virtual reality system of the virtual ambulatory environment brain imaging system in accordance with various embodiments of the present disclosure.
Figure 5B:
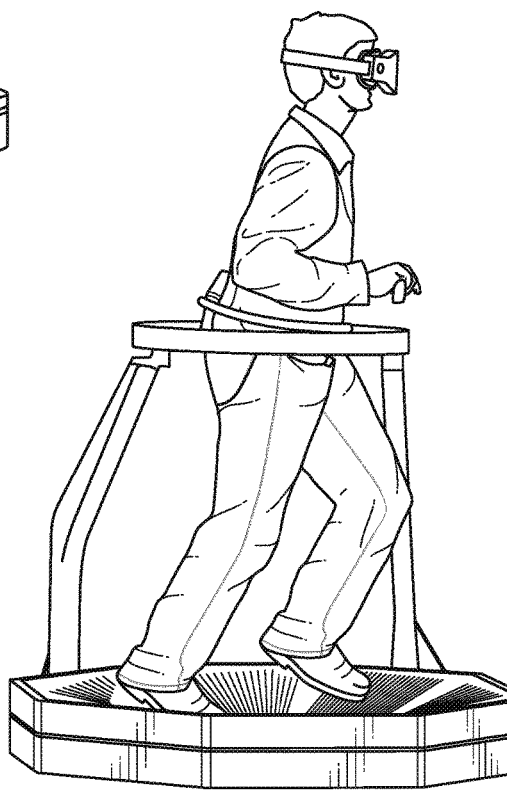
Figure 5C:
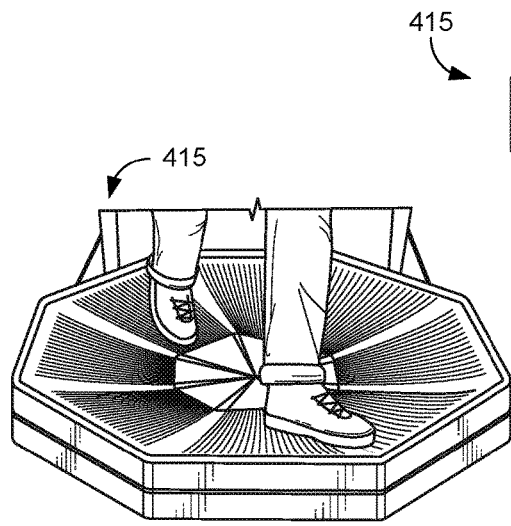

A standard treadmill or mobility platform 415 can be used to allow the subjects or patients to be in motion or in various positions during the imaging. The mobility platform can allow the subject 106 to physically move and/or respond to the various stimuli while remaining in the same location. For example, the mobility platform 415 can include, e.g., a treadmill to allow the subject 106 to walk and/or run in place, as well as other safety structures for protection of the subject 106. The mobility platform 415 can also be configured to monitor the position and/or movement of the subject or patient 106 and provide feedback to the VR control system 412 and/or the mobile brain imager 100. Referring to FIGS. 5A-5C, shown are images of an example of a mobility platform 415 (Virtuix Omni natural motion interface) that includes a concave surface that enables the subject 106 to walk and/or run with a natural gait. The position and/or pressure of the subject's feet (or other portion of the body) on the surface can be detected by the mobility platform 415 and communicated to the VR control system 412. A harness can be secured to the mobility platform to provide support for the subject 106.

The effect of a virtual ambulatory environment on the functioning of the brain can be close to the stimulation experienced by the human brain during real world situations, while eliminating logistical issues and improving safety during imaging with the subject 106 in motion. The mobile brain imager 100 offers a low-dose capability that may be attributed to the imaging photodetector modules 103 being placed much closer to the patient's head, which increases the geometrical detection efficiency over that of a standard PET ring in a PET/CT combo. With size and efficiency optimization, the mobile brain imager 100 may operate at about 10% of the standard dose used in PET/CT scans. This dose level allows multiple PET scans to be performed within a short period of time. Images can be reconstructed using an algorithm that uses 1×1×1 millimeter voxels and iterative reconstruction for 10 iterations. Reconstructed images can be displayed using imaging software (e.g., ImageJ public domain software and/or MIM professional software) to compare images of the mobile brain imager 100 with PET/CT images.

To achieve high efficiency (and low injection dose), compactness, low weight, and low cost, the tight geometry of the imaging photodetector modules 103 surrounding the patient's head is needed, but introduces larger cracks in angular coverage between the photodetector modules 103. This limits the angular sampling, resulting in increased response non-uniformities in the reconstructed images. Correction algorithms can be used to minimize the effects of the non-uniformities, improving the level of image normalization, and enhancing overall image quality. Adding photodetector modules 103 can also reduce the angular geometry coverage effects.

Testing with the mobile brain imager 100 of FIG. 3A, which includes a ring of twelve imaging photodetector modules 103, was carried out. Uniformity correction was performed by image division of the reconstructed 2D slices obtained from an imaged object (e.g., a phantom or a patient's brain) based upon experimentally obtained slice images of a cylindrical "flood" phantom. The "flood" phantom was a cylinder covering the entire useful field of view of the imager, which was filled with a F18-FDG water solution with a uniform volume concentration of radioactivity. The uniformity correction can account for the geometrical response matrix of the detectors, as well as for the bulk of the 511 keV annihilation gamma absorption effects. The geometrical response matrix can include a detector response that accounts for the fact that the imaging photodetector modules 103 have gaps between the modules 103. In addition, the detector response can correct for imperfections in the imaging photodetector modules 103 and/or imperfections caused by errors in the calibration procedure. It was established that both the flood cylinder and the brain are primarily composed of water, and produced very satisfactory normalization results.

For uniformity calibration and "flood" correction, a 185 mm diameter thin-wall acrylic cylinder was placed inside a ring of PET imaging photodetector modules 103 and filled with an $^{18}$F water solution of uniform concentration. Data was then collected (for four hours) to attain high image statistics. Images of phantoms and patients 106 were collected for much shorter times. Division of the object images by the flood images obtained with the above flood phantom, resulted in uniform and artifact-free corrected images. Prior to imaging patients 106, operation of the mobile brain imager 100 was studied with many different phantoms of different sizes. The images were reconstructed with absorption correction and then "normalized" by the system response from a uniform cylinder "flood" phantom.

Four consenting patients 106 were imaged under approved institutional IRB protocol, following the patient imaging with the whole body mCT PET/CT from Siemens. The patients 106 (all male) were cancer patients requiring whole body PET/CT. An additional brain scan is an intrinsic part of the regular diagnostic patient workout. Imaging with the mobile brain imager 100 was performed after the PET/CT scans and was divided into four components: (1) fast 30 sec scan, (2) 3 min. scan, (3) 10 min. scan, and (4) 1 min. scan with patient intentionally turning his head left and right by an angle of about +/−45 deg. The last 1 min. scan was intended to demonstrate that imaging could be performed while the subject's head was freely moving. Two of the four patients 106 were imaged immediately following the PET/CT scan, and other two patients 106 were imaged after a 4-plus hour waiting period following the whole body PET/CT scan.

Figure 6:
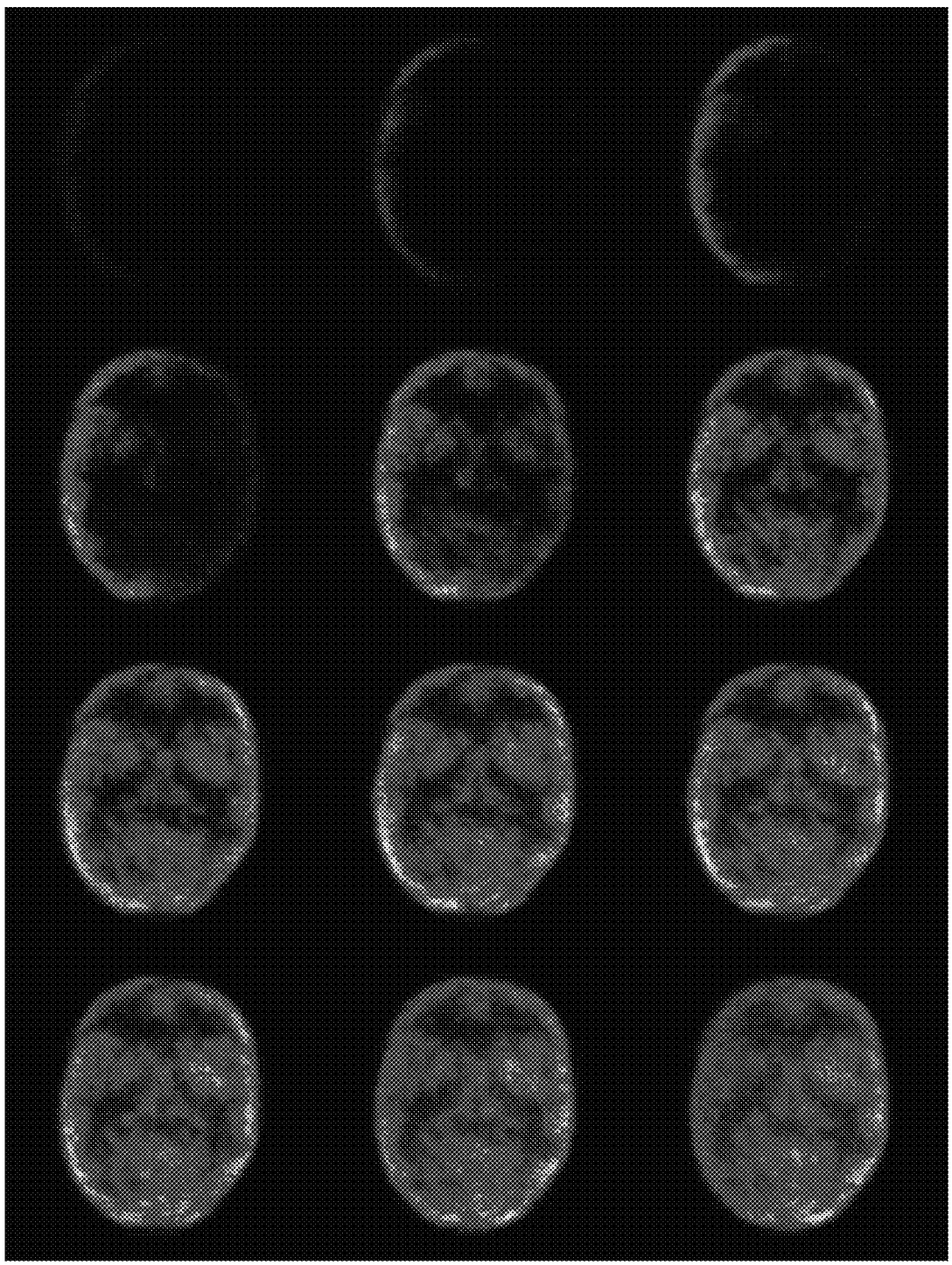
FIG. 6 shows a series of multi-slice reconstructed images of a multi-compartmental Hoffman brain phantom obtained with the mobile brain imager of FIG. 3A in accordance with various embodiments of the present disclosure.

Referring to FIG. 6, shown is a series of multi-slice reconstructed images of a multi-compartmental Hoffman brain phantom obtained with the mobile brain imager 100. The multi-compartmental Hoffman brain phantom was filled with uniform volume activity (total activity in the phantom of about 50 microCurie). The series includes twelve reconstructed 1 mm slices through the brain phantom. The images show that an object of the size of a human brain can be imaged with the mobile brain imager 100, with good spatial resolution (about 2.5 mm FWHM). The images of FIG. 6 demonstrate good uniformity of imaging in the whole phantom, despite the tight imaging geometry of the imaging photodetector modules 103.

With respect to the patient images, the imaging sessions for the first pair of patients 106 suffered from the high rate problems manifesting themselves in rate-induced DC shifts in the signal outputs of the imaging photodetector modules 103 and ultimately resulting in image distortions and artifacts that were not software correctable. The data acquisition system was capable of accepting all incoming event rates, but the rate issue was in the solid-state SiPM sensors and the associated electronics. The second pair of patients 106 was imaged 4+ hours after imaging with the PET/CT. The obtained images were of sufficient quality to analyze and compare with the PET/CT images of the patient's head and the selected results are presented here in FIGS. 7A-9B.

Figure 7A:
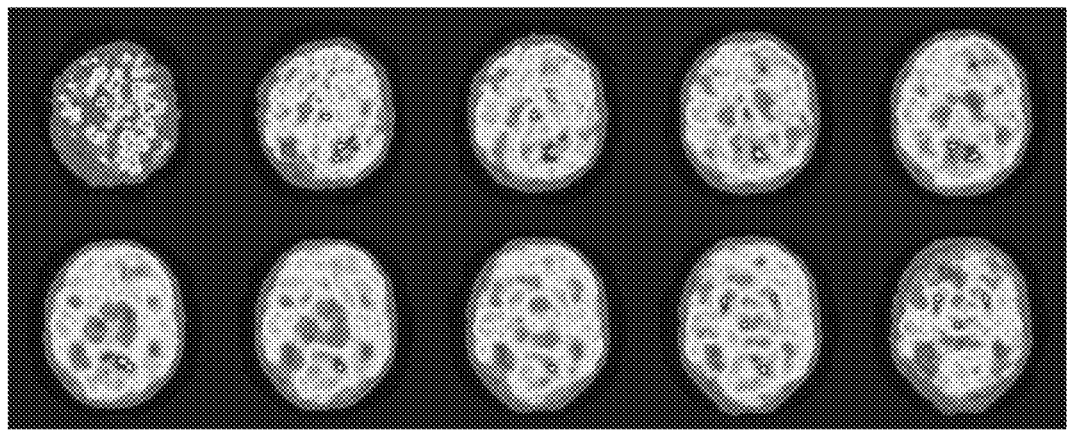
FIGS. 7A-7B, 8A-8B and 9A-9B show examples of brain images of a patient in accordance with various embodiments of the present disclosure.
Figure 7B:
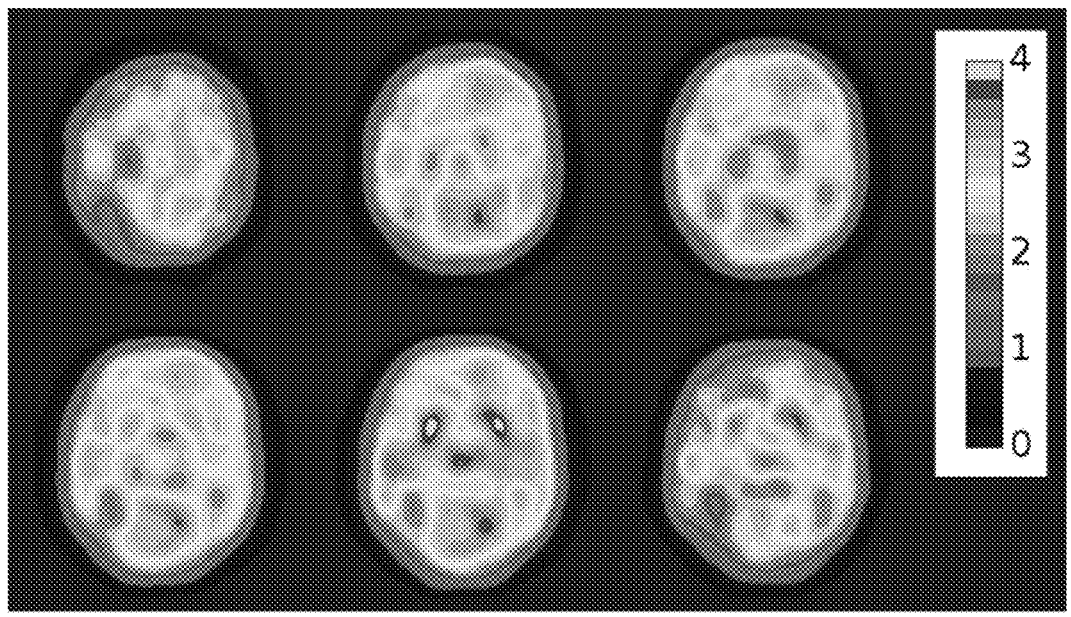

FIG. 7A shows human brain images acquired in a 600 sec scan of a patient 106 using the mobile brain imager 100. The images illustrate PET slices in 4 mm increments, with a 4 mm FWHM resolution. FIG. 7B shows clinical patent images of 8 mm slices filtered with equivalent 8 mm FWHM resolution.

Figure 8A:
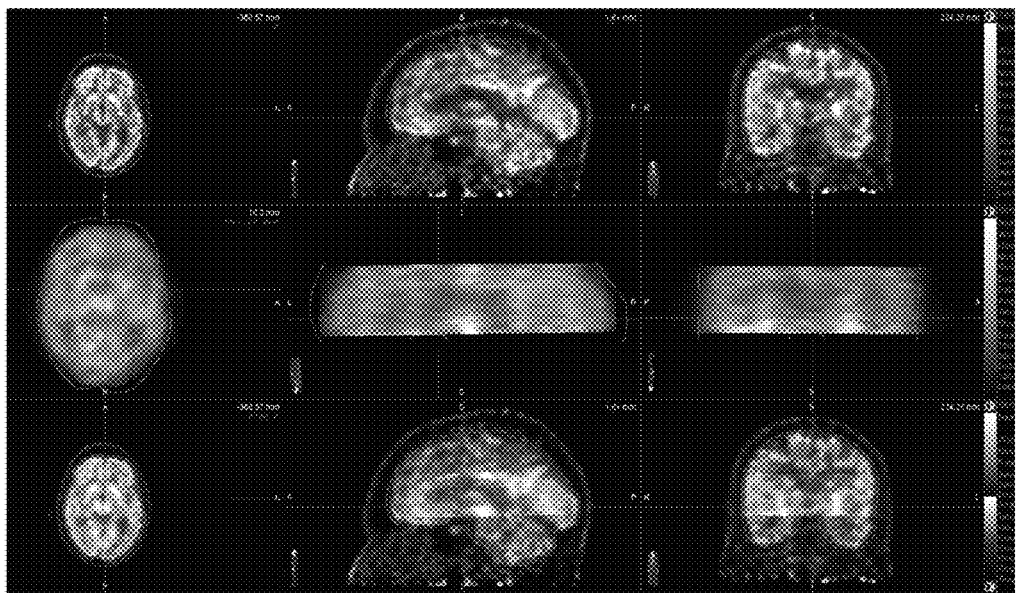
Figure 8B:
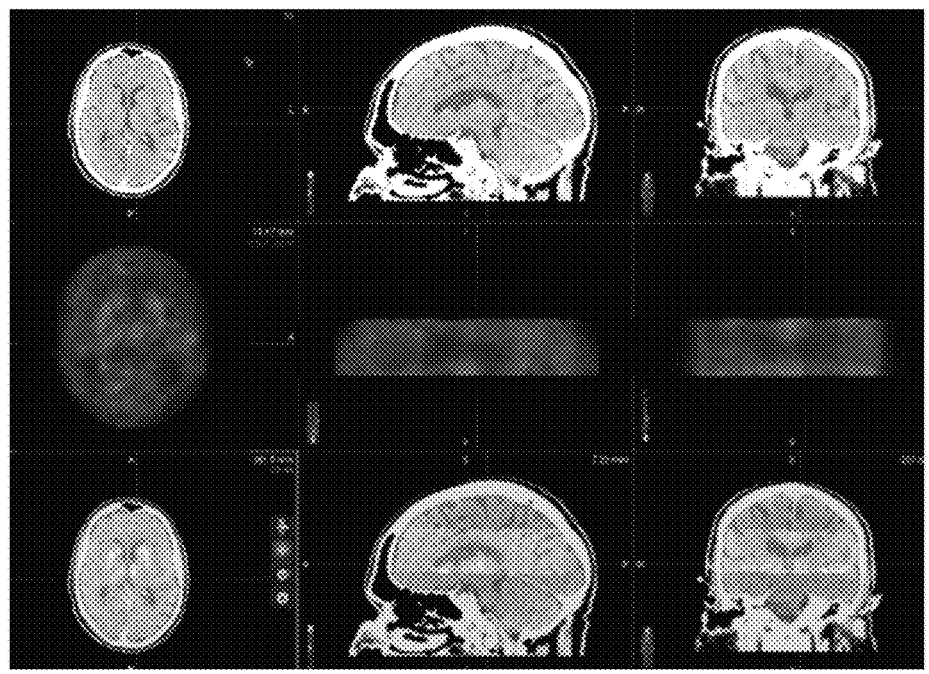

FIG. 8A shows representations of PET/CT images (top row) and mobile brain imager 100 images (middle row) from a patient 106. Though the images from the mobile brain imager 100 have poorer quality (primarily due to limited image processing), the structures observed in the mobile brain imager 100 images correlate well with the PET/CT images (as can be seen from the overlaid images in the bottom row). The images from the mobile brain imager 100 are missing some front and back edge parts of the head due to the tight placement of the imaging photodetector modules 103 on the patient's head. In addition, some differences may be attributed to obtaining the images with the mobile brain imager 100 more than 4 hours after the PET/CT scan. FIG. 8B shows CT images alone (top row), mobile brain imager 100 images (middle row), and overlaid images (bottom row) from the same patient of FIG. 8A, but with a different reconstruction slice.

Figure 9A:
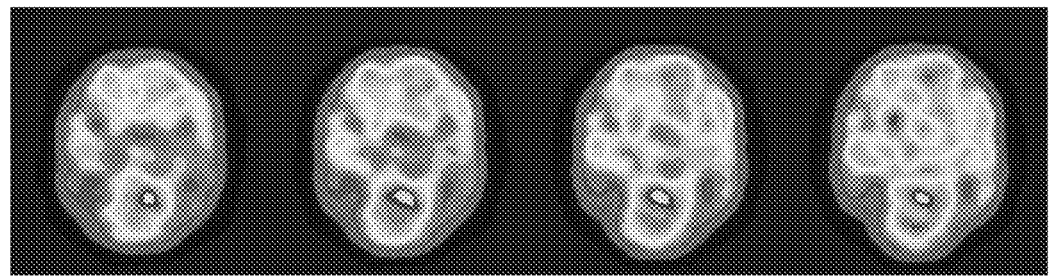
Figure 9B:
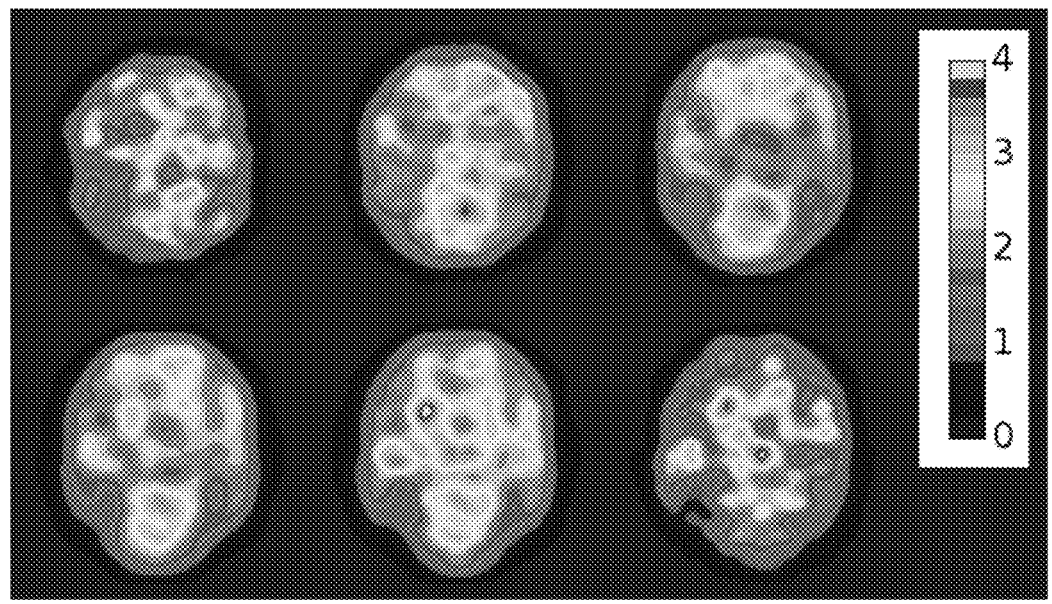

Referring now to FIG. 9A, shown are images of four central 4 mm slices that were obtained from a patient 106 with a 60 sec scan using the mobile brain imager 100 while the patient 106 was turning his head left and right by about +/−45 deg. The images demonstrate that the main F18-FDG uptake features remain stable despite a substantial head movement during the scan. The effective post-filtering resolution is 8 mm FWHM. FIG. 9B shows six 8 mm slices obtained from a second patient 106 with a 60 sec scan using the mobile brain imager 100 while the patient 106 was turning his head left and right by about +/−45 deg. In this case, the mobile brain imager 100 was placed higher on the patient's head, resulting in images of the top of the patient's head (left top). The effective post-filtering resolution is again 8 mm FWHM.

A wearable mobile brain imager 100 has been demonstrated by the human brain PET scans obtained using the device. Mounting the mobile brain imager 100 on the head of the patient 106 was possible with proper mechanical support. The results demonstrate the feasibility of a two-three ring mobile brain imager 100, which could operate with a reduced injected dose of a radiolabeled compound. Scan times as short as 60 seconds or 30 seconds obtained images that show the key features of the distribution pattern of the F18-FDG uptake. Taking into account that the images were taken 4 hours-plus after injection, and that the standard PET/CT images were obtained in 300 seconds, it may be feasible to lower the injected dose by a factor 10 or more for uptake pattern imaging.

The mobile brain imager 100 cam be beneficial in the investigation of recovery from stroke, as well as other brain conditions that impact functionality of the brain in upright (sitting or standing) position. In addition, while dementia patients do not need upright imaging, they often have problems maintaining steady head position during PET scans of their brain. The wearable and naturally co-registered (and low-dose) PET imager can be a good option for these patients.

Mobile brain imagers 100 with additional rows or hemispherical coverage can provide more brain coverage and increased detection efficiency. Increasing the ring diameter to 24-25 cm from the current 21 cm can also avoid cutting the periphery of the objects in the reconstructed images, as observed in FIG. 8A. The LYSO scintillator may also be replaced by BGO in some embodiments, or a TOFPET option with LYSO or similar fast scintillator may be implemented. Patient comfort should also be considered with all designs.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A system for virtual ambulatory environment brain imaging, comprising:
   a mobile brain imager configured to obtain positron emission tomography (PET) scans of a freestanding subject in motion, where the mobile brain imager comprises an array of imaging photodetector modules that are distributed about, secured to, and supported by a head of the freestanding subject while the PET scans are obtained;
   a support system configured to suspend the mobile brain imager, where the support system allows freedom of movement of the freestanding subject, where the support system is a mobile robotic support system configured to adjust its position based upon movement of the freestanding subject or a self-contained backpack support system; and
   a virtual reality (VR) system configured to provide one or more stimuli to the freestanding subject during the PET scans.

2. The system of claim 1, wherein the array of imaging photodetector modules are distributed in a cylinder about the head of the freestanding subject.

3. The system of claim 1, wherein the array of imaging photodetector modules extend over eyes of the freestanding subject.

4. The system of claim 3, wherein the mobile brain imager comprises compact goggles configured to provide visual stimulation to the freestanding subject, the compact goggles positioned between at least a portion of the photodetector modules and the eyes of the freestanding subject.

5. The system of claim 1, wherein the support system is configured to provide a counterbalance force to neutralize the weight of the mobile brain imager.

6. The system of claim 5, wherein the support system allows the head of the freestanding subject to move with six degrees of freedom when wearing the mobile brain imager.

7. The system of claim 1, wherein the VR system comprises a VR control system configured to control at least one virtual interface configured to stimulate the freestanding subject.

8. The system of claim 7, wherein the at least one virtual interface comprises a visual interface, a tactile interface, or both.

9. The system of claim 7, wherein the VR control system controls the at least one virtual interface in response to movement of the freestanding subject.

10. A system for virtual ambulatory environment brain imaging, comprising:
    a mobile brain imager configured to obtain positron emission tomography (PET) scans of a freestanding subject in motion, where the mobile brain imager comprises an array of imaging photodetector modules that are distributed about, secured to, and supported by a head of the freestanding subject while the PET scans are obtained;
    a support system configured to suspend the mobile brain imager, where the support system allows freedom of movement of the freestanding subject; and
    a virtual reality (VR) system configured to provide one or more stimuli to the freestanding subject during the PET scans, where the VR system comprises:
      a VR control system configured to control at least one virtual interface configured to stimulate the freestanding subject, and
      a mobility platform in communication with the VR control system, the mobility platform configured to support the freestanding subject and monitor movement of the freestanding subject.

11. The system of claim 10, wherein the array of imaging photodetector modules are distributed in a hemisphere about the head of the freestanding subject.

12. The system of claim 10, wherein the support system is a self-contained backpack support system.

13. The system of claim 10, wherein the at least one virtual interface further comprises a visual interface, a tactile interface, or both.

14. The system of claim 10, wherein the VR control system controls the at least one virtual interface in response to movement of the freestanding subject.

15. The system of claim 10, wherein the support system allows the head of the freestanding subject to move with six degrees of freedom when wearing the mobile brain imager.

16. A method for virtual ambulatory environment brain imaging, comprising:
   securing a mobile brain imager to a head of a freestanding subject, the mobile brain imager comprising an array of imaging photodetector modules distributed about and supported by the head of the freestanding subject, where the mobile brain imager is suspended by a mobile support system that adjusts position in response to movement of the freestanding subject;
   providing stimulation to the freestanding subject through a virtual reality (VR) system; and
   obtaining a positron emission tomography (PET) scan of a brain of the freestanding subject using the mobile brain imager while the freestanding subject is moving in response to the stimulation from the VR system.

17. The method of claim 16, wherein the mobile brain imager comprises compact goggles configured to provide visual stimulation to the freestanding subject, the compact goggles positioned between at least a portion of the photodetector modules and eyes of the freestanding subject.

18. The method of claim 16, wherein the support system provides a counterbalance force to neutralize at least a portion of a weight of the mobile brain imager and supports connections to the mobile brain imager.

19. The method of claim 16, wherein a VR control system controls the stimulation provided to the freestanding subject in response to movement of the freestanding subject.

20. The method of claim 19, wherein the stimulation provided to the freestanding subject comprises tactile stimulation.

* * * * *